United States Patent [19]

Slough et al.

[11] Patent Number: 4,468,613

[45] Date of Patent: Aug. 28, 1984

[54] APPARATUS FOR DETECTING CORROSION RATE

[75] Inventors: Carlton M. Slough, Spring; Stephen A. Cruser, Houston, both of Tex.

[73] Assignee: Texaco Inc., White Plains, N.Y.

[21] Appl. No.: 325,536

[22] Filed: Nov. 27, 1981

[51] Int. Cl.³ ............................................. G01N 27/00
[52] U.S. Cl. ..................... 324/71.2; 324/54; 324/51; 324/65 CR; 324/65 R
[58] Field of Search ............... 324/51, 54, 65 R, 65 P, 324/65 CR, 71.2, 439, 446, 448, 450; 200/61.03, 61.04; 340/605, 626

[56] References Cited

U.S. PATENT DOCUMENTS

| | | | |
|---|---|---|---|
| 1,962,168 | 7/1930 | Andrus | 340/626 |
| 2,993,366 | 7/1961 | Birkness | 324/439 |
| 3,222,920 | 12/1965 | Marsh et al. | 324/65 CR |
| 3,922,515 | 11/1975 | Meisenheimer, Jr. | 340/605 |
| 4,306,127 | 12/1981 | Payne | 200/61.04 |
| 4,313,042 | 1/1982 | Ehrhart | 200/61.04 |

Primary Examiner—Michael J. Tokar
Assistant Examiner—B. J. Kelley
Attorney, Agent, or Firm—Robert A. Kulason; Carl G. Ries; Henry C. Dearborn

[57] ABSTRACT

A method of measuring the rate of corrosion of a metallic structure that is subjected to a corrosive ambience. It subjects a thin metallic enclosure to the same ambience as the metallic structure is subjected to. The thin enclosure is subjected to the ambience on one side, while it maintains a different condition on the other side of the enclosure. Then, it detects a change when the different condition is no longer maintained due to the thin enclosure having corroded through.

A probe for detecting the corrosion rate of metallic piping or the like. It includes a thin metal enclosure mounted with one side subjected to the corrosive ambience acting upon the piping. There is means for subjecting the other side of the thin enclosure to a condition that is different from that of the corrosive ambience. And, there is a means for detecting a change of the different condition when the thin metal enclosure corrodes through.

7 Claims, 3 Drawing Figures

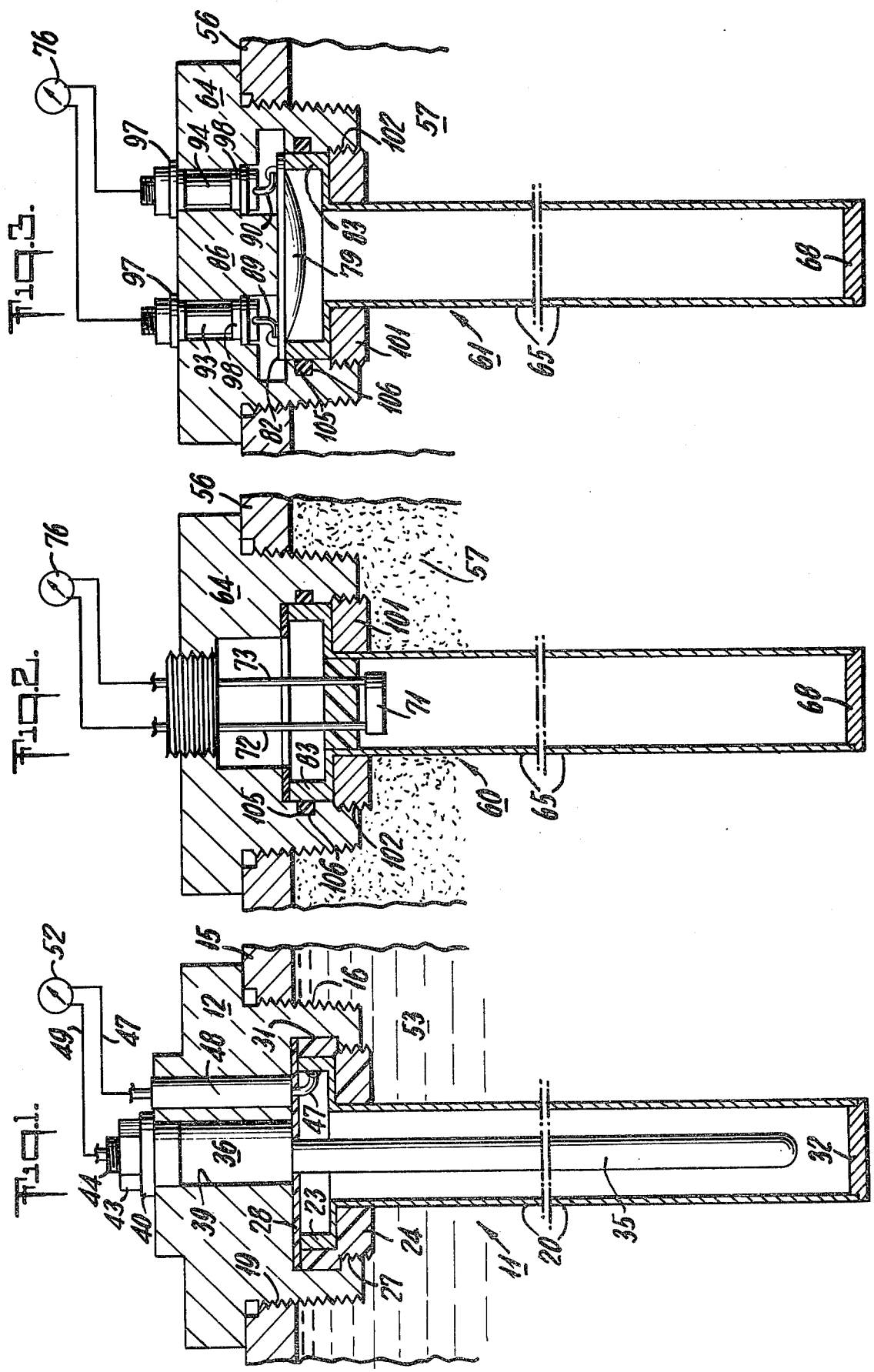

APPARATUS FOR DETECTING CORROSION RATE

BACKGROUND OF THE INVENTION

1. Field of the Invention

This invention concerns corrosion measurement in general. More specifically it concerns a method and/or apparatus for measuring the rate of corrosion of metallic structures that are subjected to a corrosive ambience.

2. Description of the Prior Art

It has long been known that internal pitting and other forms of accelerated corrosion will result in rapid failure of piping, tanks and other steel structures, all without warning. Heretofore, visual inspection has been the only means of detecting the pitting or other corrosive conditions, and such inspection requires system shut down and disassembly which, or course, is costly and time consuming.

While there is an old U.S. Pat. No. 1,962,168 issued June 12, 1934 to Orin E. Andrus, that patent deals with a lined pressure vessel. It has provision for detecting a leak (if it should occur) through the lining of such a vessel. The arrangement of that patent makes use of the fact that the pressure in the vessel is well above atmospheric. And, if there should be a leak in the lining, the pressure increase would be detected by having small holes that communicate with the space between the high pressure thick wall and the liner within. Clearly, the Andrus patent has no concern for, nor any recognition of a measurement of corrosion. Rather, it intends that any damage to the liner would be detected before the leak could cause extensive injury.

On the other hand, the applicants' invention provides for a thin-walled enclosure that has means for detecting when such thin wall has corroded through. The time element is of concern, so that the rate of corrosion will be detected. The rate detected is based upon a predetermined known thickness of the thin wall, so that the wall of the protected structure will not as yet have been corroded through.

SUMMARY OF THE INVENTION

Briefly, the invention concerns a method of measuring rate of corrosion of a metallic structure subjected to a corrosive ambience. The method comprises subjecting a thin metallic enclosure to said corrosive ambience on one side thereof, and maintaining a different condition on the other side of said thin enclosure relative to said corrosive ambience. It also comprises detecting a change when said different condition is no longer maintained because said thin metallic enclosure has corroded through.

Again briefly, the invention concerns a probe for detecting corrosion rate of metallic piping, tanks and the like that are subjected to a corrosive ambience. It comprises a thin metal enclosure adapted for being mounted with one side thereof subjected to said corrosive ambience, and means for subjecting the other side of said thin metal to a condition different from said ambience. It also comprises means for detecting a change of said different condition when said thin metal corrodes through.

Again briefly, the invention concerns a probe for detecting corrosion rate of metallic piping, tanks and the like subjected to a corrosive gaseous ambience. The probe comprises a body member having means for mounting on said piping, and a thin cylindrical metal enclosure mounted on said body member and adapted for extending into said piping. The said gaseous ambience is inside said piping and has a pressure greater than the pressure inside said cylindrical enclosure. It also comprises a pressure switch supported by said body member and subjected to said pressure inside said cylindrical enclosure, and electrical circuit means in said body member of making connections to said pressure switch. The said pressure switch is open when subjected to said pressure inside said cylindrical enclosure and closed when subjected to said ambience greater pressure. It also comprises means adapted for electrical connection to said circuit means to indicate when said pressure switch is closed.

Once more briefly, the invention concerns a probe for detecting corrosion rate of metallic piping, tanks and the like subjected to a corrosive liquid ambience. The said liquid is electrically conductive and the probe comprises a body member having means for mounting on said piping and a thin metal cylindrical enclosure mounted on said body member and adapted for extending into said liquid ambience contacting the outside of said enclosure. It also comprises an elongated conductive material electrode extending coaxially inside of said cylindrical enclosure, and means for insulating said electrode from said enclosure. It also comprises electrical circuit means for determining the conductivity between said electrode and said enclosure whereby an increase in said conductivity will indicate that said thin enclosure has corroded through admitting said ambient liquid.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 1 is a schematic longitudinal cross-section, illustrating one embodiment of a probe according to the invention;

FIG. 2 is a schematic cross-sectional view illustrating a modification that is applicable to a probe for use with gaseous ambience; and FIG. 3 is another schematic longitudinal cross-section illustrating a modified type of gaseous ambience probe structure.

DESCRIPTION OF THE PREFERRED EMBODIMENTS

In many uses of piping, tanks, and other metallic and/or steel structures, they are subjected to a corrosive ambience. Prior to this invention, visual inspection of such structures has been the only practical and/or economic means for detecting such corrosion. However, since a visual inspection required the shutting down of a system involving such structure and disassembly thereof, it has been a costly and time consuming operation.

However, a method and apparatus according to this invention provides a manner of measuring the rate of corrosion in a shortened time period and under the same ambient coditions as a structure that is subjected to corrosion. Consequently, the measurement makes a determination that is protective of the structure since the corrosion rate measurement is determined in a shorter period of time than would be required to corrode through the structure. Thus, the use of a thin metallic enclosure with a known wall thickness enables one to make a determination of the time required for its thin wall to corrode through.

With reference to FIG. 1, it may be noted that the probe structure illustrated is a type that is particularly adapted for use with a liquid corrosive ambience. Thus, there is shown a probe 11 that has a body member 12 which is adapted for being fastened into a pipe 15 by having a threaded portion 16 on the body member 12. The threaded part 16 screws into a female threaded hole 19 in the pipe wall 15.

There is a thin metal cylindrical enclosure 20 that is mounted on the body member 12. It has an enlarged upper portion 23 that is held in place by an electrically insulating material collar 24 which has external threads for matching with an internally threaded socket 27 on the lower portion of the body member 12. It will be appreciated that electrical insulation of the metallic enclosure 20 from the body member 12 might be accomplished in various other ways (not shown) that would suggest themselves to anyone skilled in the art.

The enlarged upper portion 23 of the enclosure 20 is securely held in contact with an insulating material disc or washer 28. Also, outside of the upper portion 23 (of enclosure 20) there is a ring made of electrically insulating material 31.

It may be noted that the thin metal walls of the enclosure 20 are constructed with a controlled predetermined thickness. And, the metal is preferably the same metal as the pipe wall 15. By predetermining the thickness of this probe wall, the rate of corrosion will be measured from the time of installation of the probe until the corrosion has penetrated through the enclosure 20.

It will be appreciated that the lower end of the enclosure 20 may be constructed in any feasible manner, e.g. by having a solid disc 32 that is welded or otherwise securely attached to create a tight end closure for the cylindrical portion 20.

There is an elongated electrically conductive material electrode 35 that is situated coaxially within the enclosure 20 and extends the full length thereof but without contacting the end disc 32. Electrode 35 has an upper larger diameter portion 36 which is adapted for being centrally mounted and spaced from the walls of a hole 39. Hole 39 is centrally located in the body member 12. At the upper end of the portion 36, there is a grommet 40 that is made of electricaly insulating material. It act with the disc 28 to hold the electrode 35 and its upper portion 36 centrally located so as to be electrically insulated from the body member 12. The electrode 35 (and 36) is secured in place by having a nut 43 which screws onto a smaller diameter threaded portion 44 of the upper end 36.

In order to determine the conductivity between the electrode 35 and the enclosure 20, there is a conductivity meter 52 which has an electrical conductor 47 connected to one terminal thereof. Conductor 47 may be welded or otherwise attached to the upper portion 23 of the enclosure 20. There is an insulating material sleeve 48 that extends through the body member 12 in order to maintain the conductor 47 insulated from the body. There is another conductor 49 which is connected to the electrode 35-36 from the upper end 44 thereof. Conductors 47 and 49 both lead to the conductivity meter 52.

It may be noted that the probe 11 is subjected to a liquid corrosive ambience 53 which is in contact with the inside of the pipe wall 15. And, it is the corrosive rate of the wall 15 which is being measured. Since the electrical conductivity of the corrosive liquid 53 is relatively high, it provides an indication of the rate of corrosion as measured by the predetermined thickness of the enclosure 20. Such rate is determined by the time it takes for the enclosure 20 to corrode through so that the ambient liquid 53 can enter the space surrounding the electrode 35. When that happens there will be a clear electrical conductivity increase indicated by the meter 52. It may be found to be worth while to evacuate the space between the electrode 35 and the inside of the enclosure 20, slightly, in order to assist the entrance of the liquid 53 when the walls of the enclosure 20 have corroded through.

It may also be noted that the probe 11 may be concurrently employed to make measurements of the effectiveness of a corrosion inhibitor. That would be done in accordance with the system described in a U.S. Pat. No. 4,266,187 issued May 5, 1981 and assigned to the same assignee as this application. Thus, to make an electrical resistance measurement of a corrosion inhibiting film on the outside of the enclosure 20, a test instrument (not shown) according to the foregoing patent would be connected between the enclosure 20 and the pipe wall 15 or the body member 12. Then, a concurrent measurement by the conductivity meter 52 may be carried out to determine when the walls of enclosure 20 have corroded through.

While the foregoing description relating to FIG. 1 contemplates the use of the same metal for the probe enclosure 20 and the electrode 35 as the pipe 15, e.g. steel, it should be noted that the probe 11 could be made with different metals for the electrode and the enclosure. These metals would be selected to provide a known voltage when immersed in the corrosive liquid, e.g. brine. And, upon failure of the enclosure 20, allowing the brine to enter, the voltage would signal that event.

It is also contemplated that the probe 11 could be constructed with a hollow thin walled element (not shown) that would enclose a battery (not shown) which is inactive when dry. Then entry of the corrosive liquid, e.g. brine, when the thin walled element had corroded through would activate the battery and so provide battery voltage as a signal.

FIG. 2 and 3 show two modifications of probe structure for detecting corrosion rate, where the corrosive ambience is a gaseous substance. Since the structures of the FIGS. 2 and 3 modifications are quite similar, the same reference numerals will be applied to the corresponding parts which are substantially the same in each modification. It may be observed that the FIG. 2 modification is somewhat more schematic than that of FIG. 3.

With reference to FIG. 2, it will be noted that there is a pipe or tank wall 56, which contains a gaseous corrosive ambience 57 therein. Attached to the wall 56 in each case there is a probe 60 (FIG. 2) and a probe 61 (FIG. 3). In both cases each probe 60 and 61 has a body member 64 that supports a thin cylindrical metal enclosure 65. Each enclosure 65 extends into the ambience 57 which is contained by the pipe or tank wall 56. The cylinder 65 in each case has a closed end 68 and the gaseous ambience 57 is at a pressure greater than the pressure inside of the enclosures 65.

In FIG. 2 there is a pressure switch 71 that is schematically indicated. It might take any feasible form. Also, there are electrical circuit connectors 72 and 73 which lead from the pressure switch 71 to a meter 76. The meter 76 may be arranged to indicate when the switch 71 is shifted from one position to another as caused by a change in pressure within the enclosure 65. A usual arrangement will be to have the pressure switch 71 open when subjected to the pressure inside of the enclosure 65 and close when subjected to the pressure of the ambient fluid 57.

In FIG. 3 there is a pressure switch 79 which may be like a commercial unit called model #1, which is manufactured by Tape Switch Corporation, Farmingdale, N.Y. 11735. Such switch is in the form of a relatively flat disc on one side, with an edge portion 82 that rests on the top edge of an upper enlarged diameter portion 83 of the enclosure 65. The switch 79 is mounted so that the flat side is up and rests against a central hub 86 of the body portion 64.

There are a pair of electrical lead wires 89 and 90 that are connected to the heads of a pair of short studs 93 and 94, respectively. The studs 93 and 94 are made of electrically conductive material and are secured in position with spacing in order to electrically insulate them from the body portion 64. There are upper and lower grommets 97 and 98 respectively in each case in order to hold the studs in position. Also, electrical circuits are connected from the studs 93 and 94 to the electric meter 76 of FIG. 3.

In both the FIG. 2 and FIG. 3 modifications, the upper enlarged portions 83 (of the enclosures 65) are fastened in place within the lower end of body members 64 by being secured with threaded collars 101 that screw into internally threaded holes 102 in the lower ends of the body members 64. Also, there are seal rings 105 in grooves 106 in order to seal the enclosures 65 from the gaseous ambient atmospheres 57.

METHOD

A method according to this invention deals with the measuring of the rate of corrosion of a metallic structure that is subjected to a corrosive ambience. The steps of such method comprise the following, not necessarily in the order recited. First, a step of subjecting one side of a thin metallic enclosure, e.g. the enclosure 20 or enclosures 65, to the corrosive ambience. Next, maintaining a different condition on the other side of the thin enclosure relative to the corrosive ambience. Then, detecting a change when the different condition is no longer maintained because the thin metallic enclosure has corroded through. Such detection might take various forms, but in the illustrated cases there are conductivity meters 52 and meters 76 which in each case indicate the change in condition.

In the illustrated cases, the different condition of the liquid ambience relative to the other side of the thin enclosure 20 is that of the conductivity of the ambient liquid compared to the enclosed interior. And, in the case of the gaseous ambience the different condition is that of pressure which is preferably lower on the interior of the enclosure that the pressure of the gaseous ambience on the outside. Thus, in both the liquid and gaseous cases, by having the enclosure made up of a predetermined thickness the rate of corrosion is measured by the time it takes for the enclosure to corrode through.

While particular embodiments of the invention have been described above in considerable detail in accordance with the applicable statutes, this is not to be taken as in any way limiting the invention but merely as being descriptive thereof.

We claim:

1. Probe for detecting corrosion rate of metallic piping, tanks and the like subjected to a corrosive gaseous ambience, comprising a body member having means for mounting on said piping, a thin cylindrical metal enclosure mounted on said body member and adapted for extending into said piping, said gaseous ambience being inside said piping and having a pressure greater than the pressure inside said cylindrical enclosure, a pressure switch supported by said body member and subjected to said pressure inside said cylindrical enclosure, electrical circuit means in said body member for making connection to said pressure switch, said pressure switch being open when subjected to said pressure inside said cylindrical enclosure and closed when subjected to said ambient greater pressure, and means adapted for electrical connection to said circuit means to indicate when said pressure switch is closed.

2. Probe for detecting corrosion rate of metallic piping, tanks and the like subjected to a corrosive liquid ambience, said liquid being electrically conductive, comprising a body member having means for mounting on said piping, a thin metal cylindrical enclosure mounted on said body member and adapted for extending into said liquid ambience contacting the outside of said enclosure, an elongated conductive material electrode extending coaxially inside of said cylindrical enclosure, means for insulating said electrode from said enclosure, and electrical circuit means for determining the conductivity between said electrode and said enclosure whereby an increase in said conductivity will indicate that said thin enclosure has corroded through admitting said ambient liquid.

3. Probe for detecting corrosion rate of metallic piping, tanks and the like subjected to a liquid corrosive ambience, comprising a thin metal enclosure adapted for being mounted with one side thereof subjected to said liquid corrosive ambience, means for subjecting the other side of said thin metal to an absence of said liquid ambience, and means for detecting a change of said different condition when said thin metal corrodes through, comprising a pair of electrodes, and means for indicating when said liquid is in contact with both said electrodes.

4. Probe according to claim 3, wherein said liquid is electrically conductive, and said indicating means is a conductivity meter.

5. Probe for detecting corrosion rate of metallic piping, tanks and the like subjected to a gaseous corrosive ambience, comprising a thin metal enclosure adapted for being mounted with one side thereof subjected to said gaseous corrosive ambience, means for subjecting the other side of said thin metal to a difference in gaseous pressure from said gaseous ambience, and means for detecting a change of said different gaseous pressure when said thin metal corrodes through.

6. Probe according to claim 5, wherein said change detecting means comprises a pressure switch, and means for detecting when said switch is actuated.

7. Probe according to claim 6, wherein said thin metal enclosure is cylindrical, said gaseous ambience is under pressure, and said pressure switch is subjected to said ambient pressure when said thin metal enclosure corrodes through.

* * * * *